(12) United States Patent
Xu et al.

(10) Patent No.: US 10,815,252 B2
(45) Date of Patent: Oct. 27, 2020

(54) BIFLAVONE-COPPER COMPLEX, PREPARATION METHOD AND APPLICATION THEREOF

(71) Applicant: NANJING FORESTRY UNIVERSITY, Nanjing (CN)

(72) Inventors: Li Xu, Nanjing (CN); Shilong Yang, Nanjing (CN); Zhong Li, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 0 days.

(21) Appl. No.: 16/487,845

(22) PCT Filed: Feb. 13, 2018

(86) PCT No.: PCT/CN2018/076736
§ 371 (c)(1),
(2) Date: Aug. 22, 2019

(87) PCT Pub. No.: WO2018/153330
PCT Pub. Date: Aug. 30, 2018

(65) Prior Publication Data
US 2020/0010483 A1    Jan. 9, 2020

(30) Foreign Application Priority Data
Feb. 22, 2017    (CN) .......................... 2017 1 0097599

(51) Int. Cl.
*A61P 35/00*    (2006.01)
*C07F 1/00*    (2006.01)

(52) U.S. Cl.
CPC .................................. *C07F 1/005* (2013.01)

(58) Field of Classification Search
CPC ..................................................... A61P 35/00
See application file for complete search history.

(56) References Cited

U.S. PATENT DOCUMENTS

2006/0024691 A1    2/2006    Benz

FOREIGN PATENT DOCUMENTS

| CN | 101857583 A | 10/2010 |
| CN | 106749344 A | 5/2017 |
| WO | 2013152313 A1 | 10/2013 |

OTHER PUBLICATIONS

American Chemical Society. Chemical Abstract Service. RN 2100253-30-1. First entered into STN/first available to public: Jun. 29, 2017. (Year: 2017).*

Uddin, Q., et al. "The biflavonoid, amentoflavone degrades DNA in the presence of copper ions." Toxicology in Vitro (2004), vol. 18, pp. 435-440. (Year: 2004).*

Lee. E, et al. Cytotoxic Activities of Amentoflavone Against Human Breast and Cervical Cancers are Mediated by Increasing of PTEN Expression Levels Due to Peroxisome Proliferator-Activated RecptorY Actiation. Bulletin of the Korean Chemical Society, 2012, 33(7), pp. 2219-2223.

Chen J. H. et al. Amentoflavone Induces Anti-Angiogenic and Anti-Metastatic Effects Through Suppression of NF-Kappa B Activation in MCF-7 Cells. Anticancer Research, 2015, 35(12):6685-6694.

Lee C. W. et al. Amentoflavone Inhibits UVB-Induced Matrix Metalloproteinase-1 Expression Through the Modulation of AP-1 Znmponents in Normal Human Fibroblasts. Applied Biochemistry and Biotechnology 2012, 166, pp. 1137-1147.

(Continued)

*Primary Examiner* — John S Kenyon
(74) *Attorney, Agent, or Firm* — Bayramoglu Law Offices LLC

(57) ABSTRACT

A biflavone-copper complex, a preparation method and application thereof are disclosed. The biflavone-copper complex has the following structural formula:

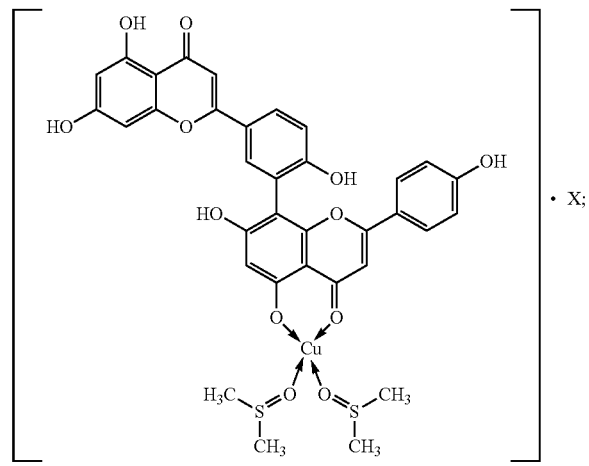

wherein, X is $NO_3^-$ or $Cl^-$. A method of preparing the biflavone-copper complex includes the following steps: dissolving a copper salt in an alcohol and then adding into a biflavone alcoholic solution, controlling pH to 5-7; under heating and stirring, performing a reaction for 2-5 h to form a precipitate; filtering the precipitate, washing the precipitate with alcohol and water, recrystallizing the precipitate using dimethyl sulfoxide as a solvent, and drying the precipitate to obtain the biflavone-copper complex. The biflavone-copper complex is used for preparing an antitumor drug and/or an antioxidant drug.

8 Claims, 11 Drawing Sheets

(56) References Cited

OTHER PUBLICATIONS

Zhang Y.P. et al. Target-Guided Isolation and Purification of Antioxidants from Selaginella Sinensis by Offline Znupling of DPPH-HPLC and HSCCC Experiments. Journal of Chromatography B, 2011, 879, pp. 191-196.

Li X.C., et al. Amentoflavone Protects against Hydroxyl Radical-Induced DNA Damage Via Antioxidant Mechanism. Turkish Journal of Biochemistry-Turk Biyokimya Dergisi, 2014, 39(1), pp. 30-36.

Zhou J., et al. Synthesis, Characterization, Antioxidative and Antitumor Activities of Solid Quercertin Rare Earth(III) Complexes. Journal of Inorganic Biochemistry, 2001, 83, pp. 41-48.

Uddin, Q. et al. The Biflavonoid, Amentoflavone Degrades DNA in the Presence of Copper Ions, Toxicology in Vitro, Aug. 31, 2004, vol. 18, pp. 435-440.

Cao Zhiquan, New Thinking About Study of Pharmacodynamic Material and Functional Mechanism in Chinese Materia Medica—Study on the Relation between Morphology and Biological Activity of Chemical Species in Chinese Materia Medica, Acta Universitatis Traditionis Medicalis Sinensis Pharmacologiaeque Shanghai, Mar. 2000, vol. 14, No. 1, pp. 36-40.

\* cited by examiner

BIFLAVONE-COPPER COMPLEX, PREPARATION METHOD AND APPLICATION THEREOF

CROSS REFERENCE TO THE RELATED APPLICATIONS

This application is the national phase entry of International Application No. PCT/CN2018/076736, filed on Feb. 13, 2018, which is based upon and claims priority to Chinese Patent Application No. 201710097599.9, filed on Feb. 22, 2017, the entire contents of which are incorporated herein by reference.

TECHNICAL FIELD

The present invention belongs to the fields of organic synthesis and medical technology, specifically relates to a biflavone-copper complex, a preparation method and an application thereof.

BACKGROUND

Biflavonoid compounds are unique chemical components of gymnosperms such as ginkgo, *Selaginella tamariscina*, etc., which have biological activities such as anti-oxidation, anti-inflammatory, anti-viral, antitumor and the like. Among them, amentoflavone (Ame) is a more common one of the biflavonoid compounds with a structural formula shown as follows.

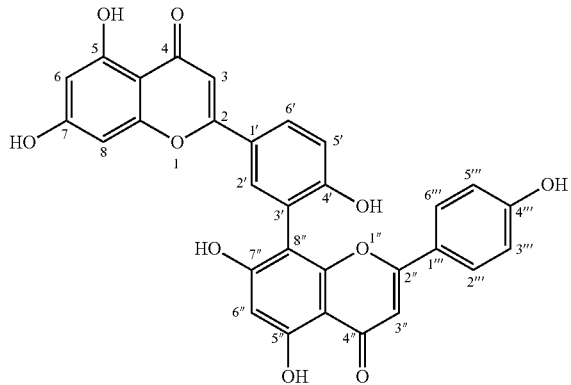

Sun et al. has researched and found that the amentoflavone can increase the expression of anti-cancer genes by activating hPPARγ, thereby achieving the effect of inhibiting breast cancer cells and cervical cancer cells (Lee E., Shin S., Lee J. et al. Cytotoxic activities of amentoflavone against human breast and cervical cancers are mediated by increasing of pten expression levels due to peroxisome proliferator-activated receptor γ activation [J]. Bulletin of the Korean Chemical Society, 2012, 33(7): 2219-2223.). Chen et al. has researched and found that the amentoflavone blocks the formation of blood vessels and the metabolism of cancer cells through inhibiting the activity of factor NF-kappa B, achieving the purpose of inhibiting the growth of tumor cells (Chen J. H., Chen W. L., Liu Y. C. Amentoflavone induces anti-angiogenic and anti-metastatic effects through suppression of NF-kappa B activation in MCF-7 cells [J]. Anticancer Research, 2015, 35(12):6685-6693.). Lee et al. has researched and found that the amentoflavone may inhibit the expression of UVB-induced matrix metalloproteinase, thereby exerting anti-oxidation and anti-radiation effects (Lee C. W., Na Y., Park N., et al. Amentoflavone inhibits UVB-induced matrix metalloproteinase-1 expression through the modulation of AP-1 components in normal human fibroblasts [J]. Applied Biochemistry and Biotechnology, 2012, 166:1137-1147.). Zhang et al. has researched and found that the amentoflavone and ginkgetin have certain antioxidant activity and strong ability to scavenge DPPH free radicals (Zhang Y. P., Shi S. Y., Wang Y. X., et al. Target-guided isolation and purification of antioxidants from Selaginella sinensis by offline coupling of DPPH-HPLC and HSCCC experiments [J]. Journal of Chromatography B, 2011, 879:191-196.). Li et al. has researched and showed that the amentoflavone has an antioxidant activity, which may effectively scavenge free radicals such as $OH^-\cdot$, $O^{2-}\cdot$, DPPH$\cdot$, ABTS$^+\cdot$, etc., and protect DNA from oxidative damage caused by $OH^-$. (Li X. C., Wang L., Han W. J., et al. Amentoflavone protects against hydroxyl radical-induced DNA damage via antioxidant mechanism [J]. Turkish Journal of Biochemistry-Turk Biyokimya Dergisi, 2014, 39(1): 30-36.).

The coordination chemistry of traditional Chinese medicines shows that complex equilibria exists in the complexes formed by the reaction between trace elements and organic compounds, so the biological activities of the original components can be exhibited. Moreover, since the synergy and antagonism that exists in trace elements, organic components, complexes and a combination thereof may weaken or enhance the biological activities of the original components, new biological activities may also be generated (Cao Zhiquan. New thoughts of studying material basis and mechanism of the efficacy of traditional Chinese medicine (1)-Study on the relationship between the specification and biological activity of chemical species in traditional Chinese medicine [J]. Journal of Shanghai University of Traditional Chinese Medicine, 2000, 14(1):36-39.). For example, Zhou et al. has researched and found that the quercetin rare earth complex has higher ability to scavenge $O_2^-\cdot$ than the quercetin. The quercetin rare earth complex can inhibit a variety of tumors, and antitumor activity thereof is higher than that of the quercetin. Wherein, the complex has a higher inhibitory effect on bladder tumor cells, while the quercetin does not have such effect (Zhou J., Wang L. F., Wang J. Y., et al. Synthesis, characterization, antioxidative and antitumor activities of solid quercetin rare earth(III) complexes [J]. Journal of Inorganic Biochemistry, 2001, 83:41-48.).

However, to date, studies on the synthesis of the biflavone complex and the biological activity thereof have not been reported.

SUMMARY

Objectives of the Present Invention: in view of the deficiencies in the prior art, one objective of the present invention is to provide an amentoflavone-copper complex, which meets the application needs of antitumor and anti-oxidation drugs. Another objective of the present invention is to provide a preparation method of the above-mentioned biflavone-copper complex. A further objective of the present invention is to provide the application of the biflavone-copper complex.

Technical Solution: in order to achieve the above objectives, the technical solution of the present invention is as follows.

The biflavone-copper complex has the following structural formula:

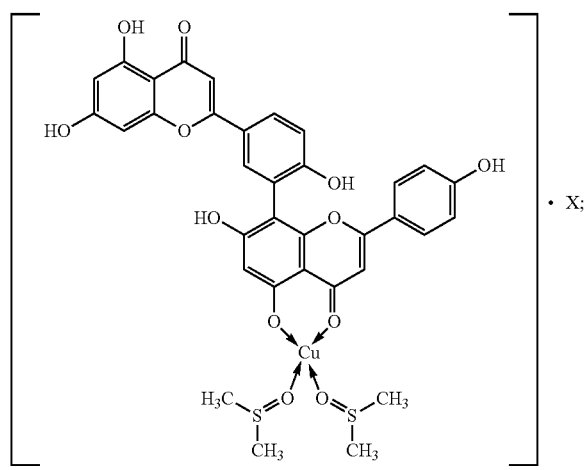

X is $NO_3^-$ or $Cl^-$.

A method of preparing a biflavone-copper complex including the following steps: dissolving a copper salt in an alcohol and then adding into a biflavone dissolved in an alcohol, controlling the pH to 5-7, under heating and stirring, performing the reaction for 2-5 h to form a precipitate, filtering the precipitate, washing with alcohol and water, recrystalling using dimethyl sulfoxide as a solvent, and drying to obtain the biflavone-copper complex.

The biflavone is an amentoflavone, but is not limited to the amentoflavone, and generally refers to biflavonoid compounds having 5-OH and 4-C=O, or having 5"-OH and 4"-C=O.

The copper salt is an alcohol-soluble copper salt such as copper nitrate, copper chloride, etc.

The solvent is ethanol, methanol and methanol/ethanol aqueous solution of various concentrations, etc.

The pH is adjusted with an alkali alcohol solution, and the alkali used in the alkali alcohol solution includes common bases such as sodium hydroxide, potassium hydroxide, aqueous ammonia, sodium ethoxide, sodium methoxide, etc.

During the reaction, the heating temperature is 30° C.-50° C., and the reaction time is 2 h-5 h.

The molar ratio of the biflavone to copper ion in the solution is 2-2.5:1.

The solvent used in the recrystallization is dimethyl sulfoxide (DMSO), and the drying method is freeze-drying, low temperature vacuum-drying, etc.

The biflavone-copper complex is used in the preparation of an antitumor drug and/or an antioxidant drug.

Beneficial Effects: compared with the prior art, the amentoflavone-copper complex is first synthesized by the method of the present invention. The antitumor activity of the Ame-Cu complex is studied by the MTT method, and the results show that the ability of the Ame-Cu complex to inhibit hepatoma cells (HepG2) and cervical cancer cells (HeLa) is stronger than that of the Ame itself. Through UV-vis absorption spectroscopy, fluorescence spectroscopy and viscosity method, it shows that the mechanism of antitumor activity of the Ame-Cu complex may be that the complex is inserted into DNA in an intercalation manner, causing apoptosis. Through the pyrogallol auto-oxidation method and ABTS method, it shows that the Ame-Cu complex has stronger ability to scavenge free radicals than the Ame itself, indicating that the antioxidant activity of the complex is stronger than that of Ame, which is conducive to the further development of the biflavonoid compounds, provides a basis for the research of new drugs and contributes to the development of human health.

DETAILED DESCRIPTION OF THE EMBODIMENTS

Figure 1:
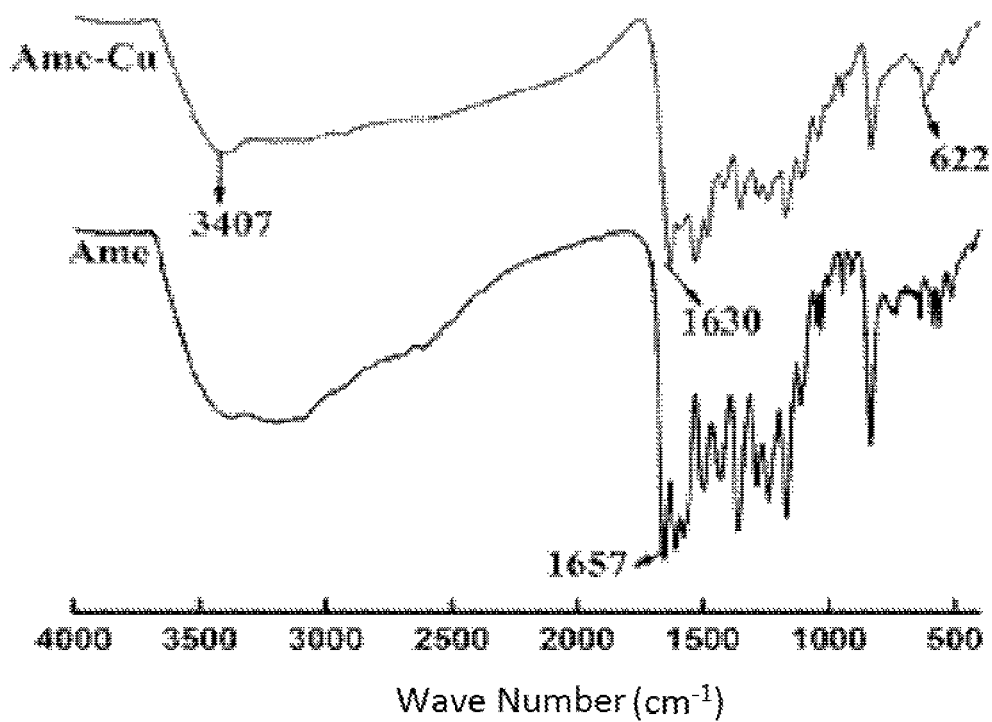
FIG. 1 is IR spectra of an Ame and an Ame-Cu complex.

The present invention will be further described below in conjunction with specific embodiments.

Embodiment 1

53.8 mg of Ame was accurately weighed and put in a round bottom flask, then the Ame was dissolved with 5 mL of ethanol; 12.1 mg of copper nitrate trihydrate was precisely weighed and dissolved with 5 mL of ethanol; the copper nitrate solution was dropwise added to the Ame solution, ethanol-ammonia (V/V, 3:1) solution was dropwise added to the reaction solution to adjust the pH to 6, and the reaction was performed at 30° C. for 4-5 h to obtain a precipitate; the precipitate was filtered, and then successively washed with ethanol and water, and recrystallized with the DMSO, and freeze-drying was performed to obtain the Ame-Cu complex.

Embodiment 2

53.8 mg of Ame was accurately weighed and put in a round bottom flask, then the Ame was dissolved with 5 mL of 90% ethanol; 12.1 mg of copper nitrate trihydrate was precisely weighed and dissolved with 5 mL of 90% ethanol; the copper nitrate solution was dropwise added to the Ame solution, ethanol-sodium ethoxide solution was dropwise added to the reaction solution to adjust the pH to 5, and the reaction was performed at 30° C. for 4-5 h to obtain a precipitate; the precipitate was filtered, and then successively washed with ethanol and water, and recrystallized with the DMSO, and freeze-drying was performed to obtain the Ame-Cu complex.

Embodiment 3

53.8 mg of Ame was accurately weighed and put in a round bottom flask, then the Ame was dissolved with 5 mL of methanol; 12.1 mg of copper nitrate trihydrate was precisely weighed and dissolved with 5 mL of methanol; the copper nitrate solution was dropwise added to the Ame solution, methanol-sodium methoxide solution was dropwise added to the reaction solution to adjust the pH to 7, and the reaction was performed at 40° C. for 3-4 h to obtain a precipitate; the precipitate was filtered, and then successively washed with methanol and water, and recrystallized with the DMSO, and freeze-drying was performed to obtain the Ame-Cu complex.

Embodiment 4

53.8 mg of Ame was accurately weighed and put in a round bottom flask, then the Ame was dissolved with 5 mL of 85% methanol; 12.1 mg of copper nitrate trihydrate was precisely weighed and dissolved with 5 mL of 85% methanol; the copper nitrate solution was dropwise added to the Ame solution, methanol-sodium methoxide solution was dropwise added to the reaction solution to adjust the pH to 7, and the reaction was performed at 50° C. for 2-3 h to obtain a precipitate; the precipitate was filtered, and then successively washed with methanol and water, and recrystallized with the DMSO, and freeze-drying was performed to obtain the Ame-Cu complex.

Embodiment 5

53.8 mg of Ame was accurately weighed and put in a round bottom flask, then the Ame was dissolved with 5 mL of ethanol; 8.5 mg of copper chloride dihydrate was precisely weighed and dissolved with 5 mL of ethanol; the copper chloride solution was dropwise added to the Ame solution, ethanol-ammonia (V/V, 3:1) solution was dropwise added to the reaction solution to adjust the pH to 6, and the reaction was performed at 30° C. for 4-5 h to obtain a precipitate; the precipitate was filtered, and then successively washed with ethanol and water, and recrystallized with the DMSO, and freeze-drying was performed to obtain the Ame-Cu complex.

Embodiment 6

53.8 mg of Ame was accurately weighed and put in a round bottom flask, then the Ame was dissolved with 5 mL of 90% ethanol; 8.5 mg of copper chloride dihydrate was precisely weighed and dissolved with 5 mL of 90% ethanol; the copper chloride solution was dropwise added to the Ame solution, ethanol-sodium ethoxide solution was dropwise added to the reaction solution to adjust the pH to 5, and the reaction was performed at 30° C. for 4-5 h to obtain a precipitate; the precipitate was filtered, and then successively washed with ethanol and water, and recrystallized with the DMSO, and freeze-drying was performed to obtain the Ame-Cu complex.

Embodiment 7

53.8 mg of Ame was accurately weighed and put in a round bottom flask, then the Ame was dissolved with 5 mL of methanol; 8.5 mg of copper chloride dihydrate was precisely weighed and dissolved with 5 mL of methanol; the copper chloride solution was dropwise added to the Ame solution, methanol-sodium methoxide solution was dropwise added to the reaction solution to adjust the pH to 7, and the reaction was performed at 40° C. for 3-4 h to obtain a precipitate; the precipitate was filtered, and then successively washed with methanol and water, and recrystallized with the DMSO, and freeze-drying was performed to obtain the Ame-Cu complex.

Embodiment 8

53.8 mg of Ame was accurately weighed and put in a round bottom flask, then the Ame was dissolved with 5 mL of 85% methanol; 8.5 mg of copper chloride dihydrate was precisely weighed and dissolved with 5 mL of 85% methanol; the copper chloride solution was dropwise added to the Ame solution, methanol-sodium methoxide solution was dropwise added to the reaction solution to adjust the pH to 7, and the reaction was performed at 50° C. for 2-3 h to obtain a precipitate; the precipitate was filtered, and then successively washed with methanol and water, and recrystallized with the DMSO, and freeze-drying was performed to obtain the Ame-Cu complex.

Embodiment 9

The products prepared in Embodiments 1-8 were characterized. The IR spectra of the Ame and the Ame-Cu complex are shown in FIG. 1. As can be seen from the figure, the Ame has a broad absorption at 2800-3500 $cm^{-1}$, which is the stretching vibration peak of the associated hydroxyl group, because intramolecular hydrogen bonds are formed between 5-OH and 4-C=O, and between 5"-OH and 4"-C=O in the Ame molecule. However, in the Ame-Cu complex, the absorption is narrowed here, and the peak shape at about 3407 $cm^{-1}$ becomes sharp, indicating that the intramolecular hydrogen bond is destroyed after the formation of the complex. The strong peak at 1657 $cm^{-1}$ in the Ame is caused by the stretching vibration of the carbonyl group, which is the characteristic absorption peak of the carbonyl group. After the complex is formed, the absorption peak moves toward the low wave number and moves to 1631 $cm^{-1}$, indicating that the carbonyl group participates in the coordination. The complex produces an absorption peak at 622 $cm^{-1}$, which is caused by the stretching vibration of Cu—O, effectively proving that oxygen atoms participate in the coordination. Therefore, it can be speculated that the carbonyl group and the hydroxyl group in the Ame participate in the coordination, and the most probable coordination sites are 5-OH, 4-C=O, 5"-OH and 4"-C=O.

Figure 2:
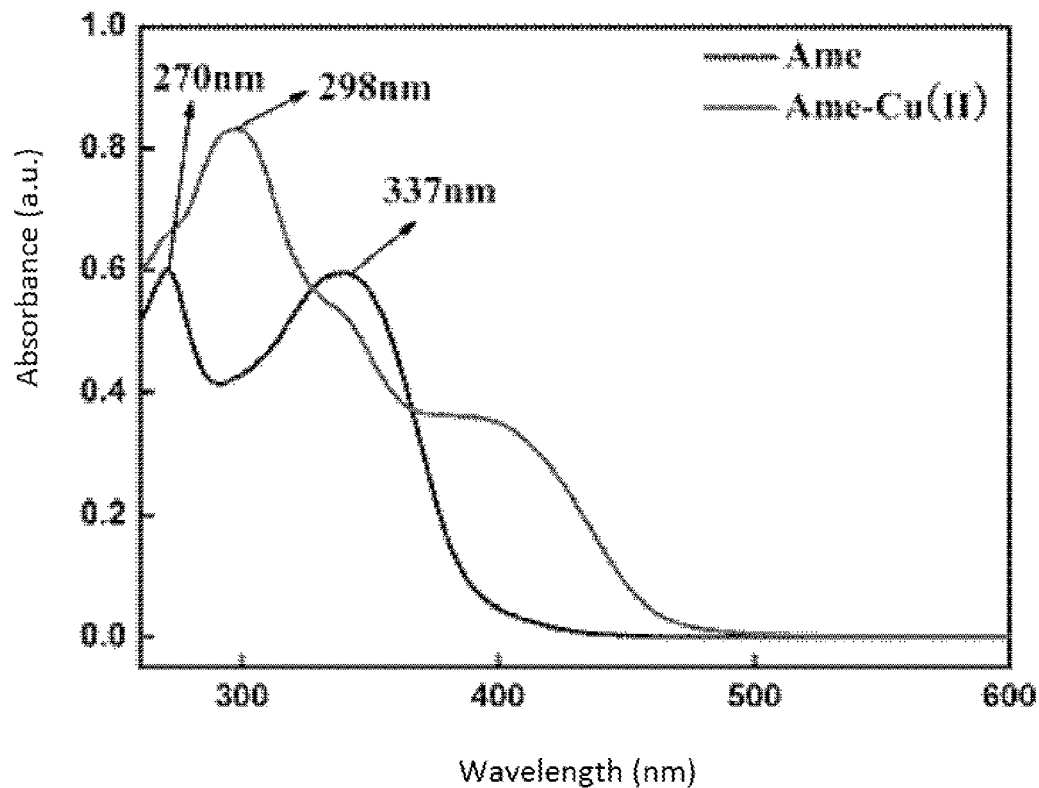
FIG. 2 is UV-vis spectra of an Ame and an Ame-Cu complex.

The UV-vis spectra of the Ame and the Ame-Cu complex are shown in FIG. 2. The Ame has two characteristic absorption peaks at 337 nm (band I) and 270 nm (band II), which are the characteristic absorptions of the flavonoid compounds. Band I and band II correspond to the UV absorptions of the cinnamyl system and the benzoyl system, respectively, which are caused by the transition of $\pi$-$\pi$*. The Ame-Cu complex produces an absorption platform between 375-450 nm, which is caused by the red shift of the band I, indicating that the cinnamyl system participates in the coordination. Although the position of the band II does not change significantly, the absorption intensity decreased relatively, and a new absorption peak is also produced at 298 nm. These phenomena indicate that the carbonyl groups of the cinnamyl system and the benzoyl system participate in the coordination. After the coordination, the conjugated system increases, the energy required for the electronic transition decreases, and $\pi$-$\pi$* transition is more likely to occur, so the band I is red-shifted. However, 4-C=O is more prone to trigger $\pi$-$\pi$* transition, so a new peak is generated at 298 nm. It can be speculated that the site where $Cu^{2-}$ forms a complex with Ame is 5-OH, 4-C=O, 5"-OH, and 4"-C=O.

In the positive ion mode, the mass spectrometric analysis of the Ame and Ame-Cu complex were carried out, and the ion structure corresponding to the molecular ion peaks on the spectrum was obtained by simulation according to mass spectrum, thus the structure of the Ame-Cu was speculated.

Figure 3:
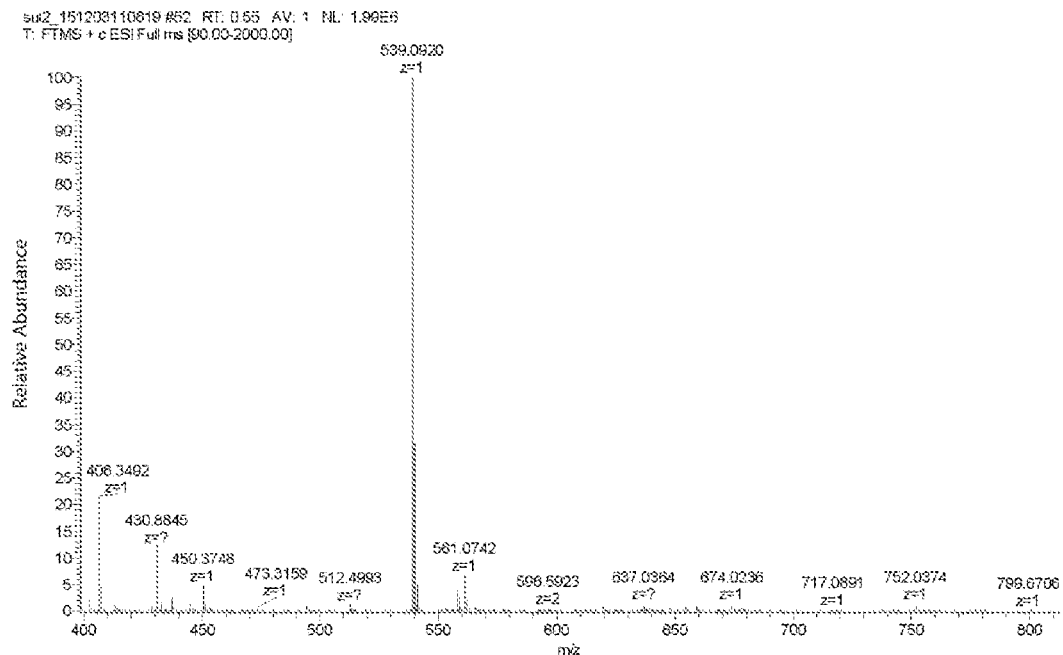
FIG. 3 is a mass spectrum of an Ame.
Figure 4A:
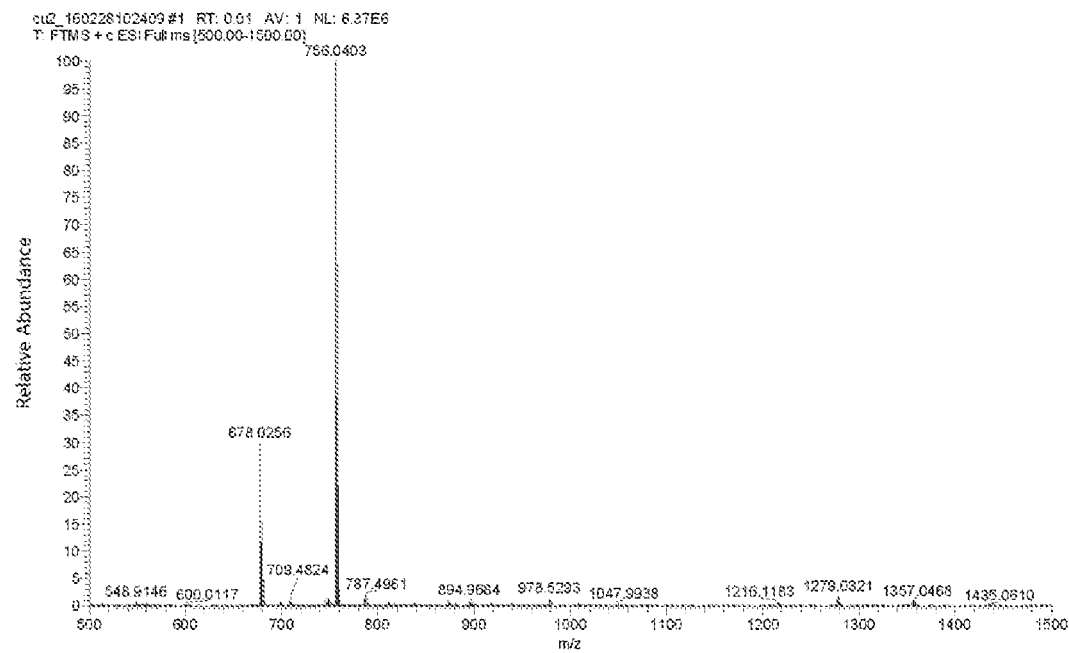
FIG. 4a is a mass spectrum of an Ame-Cu complex.
Figure 4B:
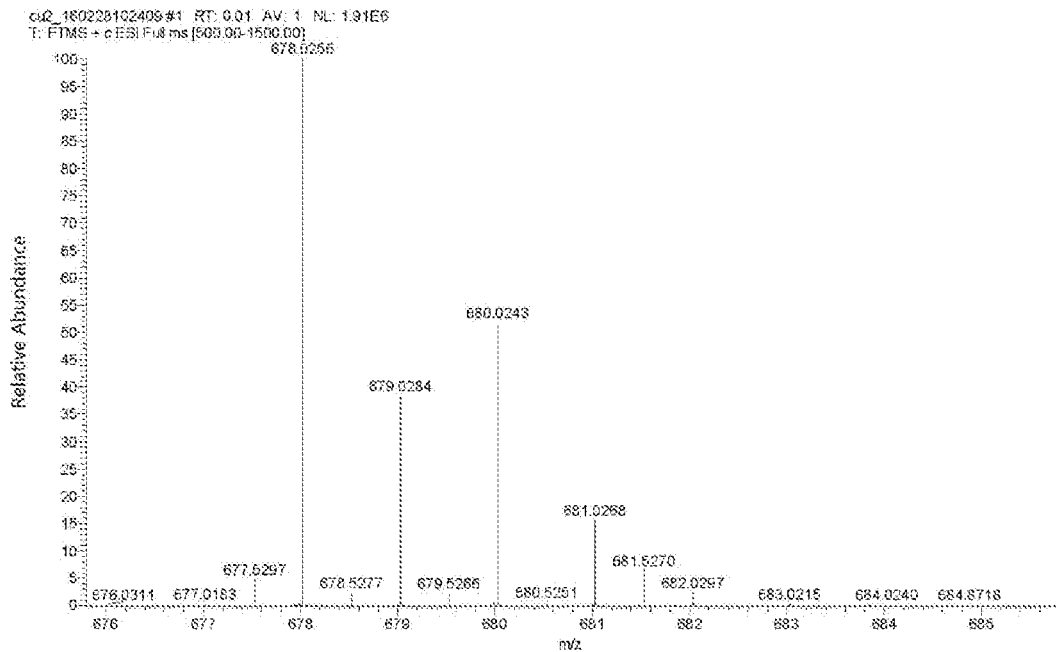
FIG. 4b is an isotope mass spectrum of an ion peak at m/z 678.0256.
Figure 4C:
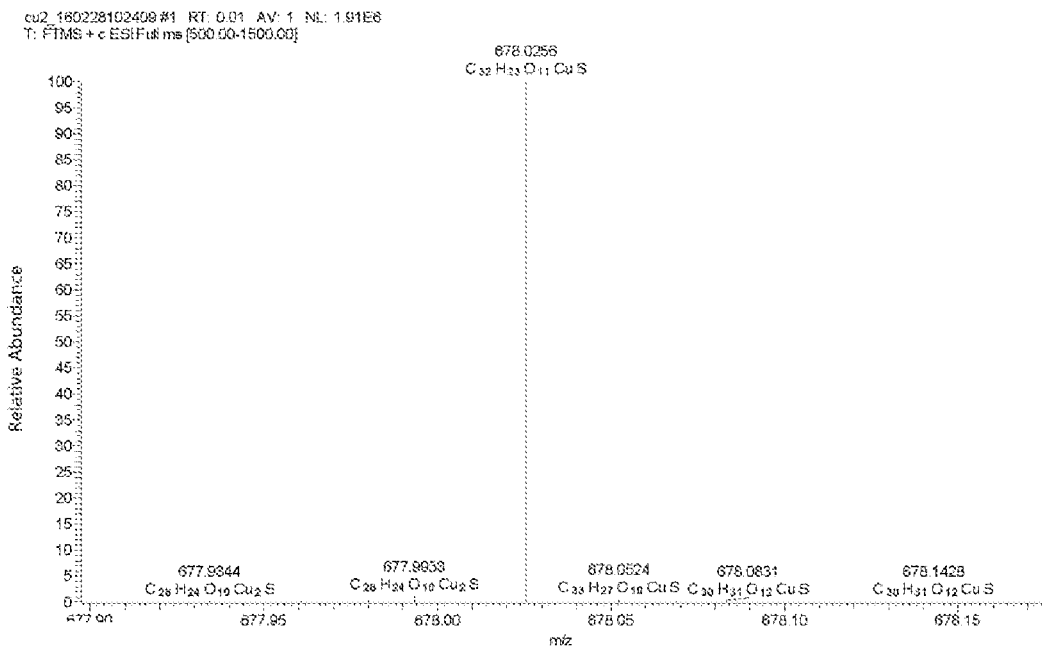
FIG. 4c is a mass spectrum of a quasi-molecule ion peak at m/z 678.0256.
Figure 4D:
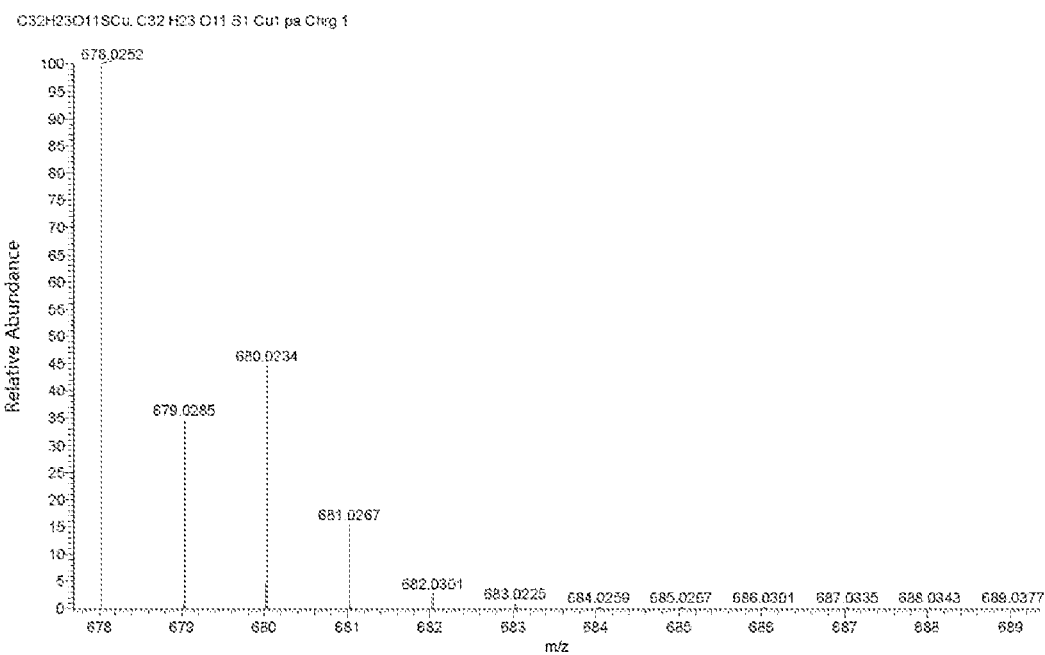
FIG. 4d is a simulated mass spectrum of $[Cu(Ame-H)(DMSO)]^+$.
Figure 4E:
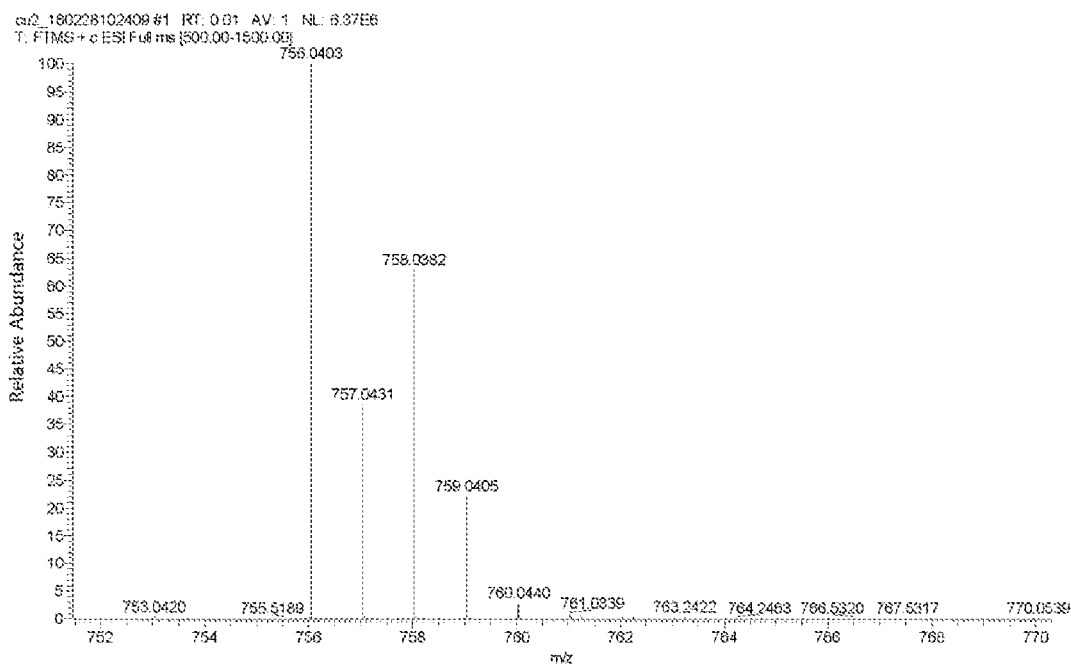
FIG. 4e is a mass spectrum of an ion peak at m/z 756.0403.
Figure 4F:
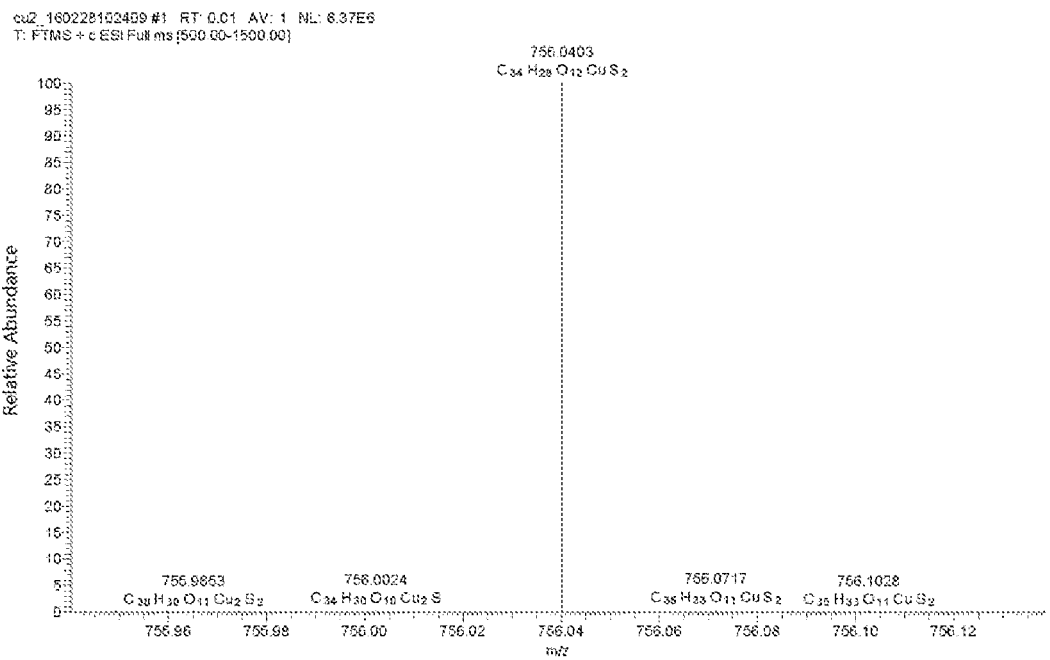
FIG. 4f is the most probable composition of m/z 756.0403.
Figure 4G:
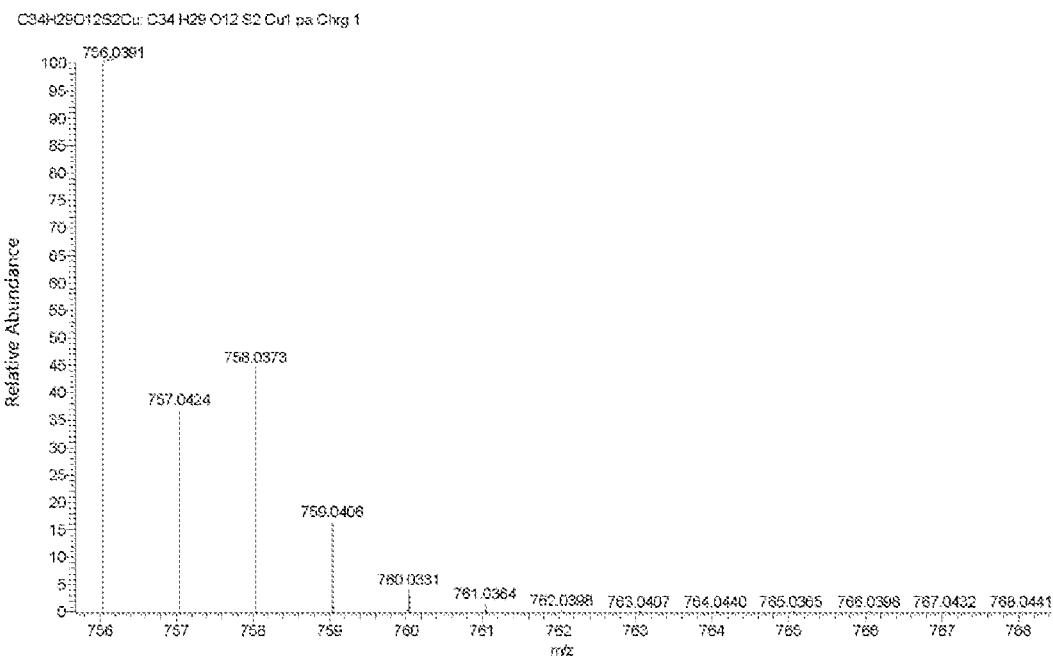
FIG. 4g is the simulated mass spectrum of $[Cu(Ame-H)(DMSO)_2]^+$.

FIG. 3 is a mass spectrum of the Ame in the positive ion mode with the quasi-molecule ion peak m/z 539.0920 belonging to [Ame+H]⁻. FIG. 4a is a mass spectrum of the Ame-Cu complex. As can be seen from the figure, the main quasi-molecule ion peaks of the Ame-Cu complex are two ion peaks respectively with a positive charge, which are m/z 678.0256 and m/z 756.0403, respectively. FIG. 4b is an isotope mass spectrum of the ion peak m/z 678.0256, it can be seen that the isotope peaks of the ion peak m/z 678.0256 are m/z 679.0284, m/z 680.0243, m/z 681.0268, and m/z 682.0297, and the molecular weights of adjacent ion peaks differ by 1.0028, 0.9959, 1.0025, and 1.0029, respectively, thereby confirming that the ion peak carries a positive charge. It can be seen from the IR spectrum and the UV-vis spectrum that the coordination sites where the Ame forms complex with $Cu^{2+}$ are 5-OH, 4-C=O, 5"-OH and 4"-C=O. Since the solvent for recrystallization and dissolution of the complex is DMSO, DMSO contains an oxygen atom and a sulfur atom, which has a strong coordination ability and is difficult to ionize, the complex may contain DMSO, thus speculating that the quasi-molecule ion peak m/z 678.0256 belongs to [Cu(Ame-H)(DMSO)]⁺. The elemental composition is $C_{32}H_{23}O_{11}CuS$, which is consistent with the possible elemental composition of the quasi-molecule ion peak m/z 678.0256 (FIG. 4c). Moreover, [Cu(Ame-H)(DMSO)]⁺ was simulated by mass spectrometry simulation software to obtain the simulated mass spectrum as shown in FIG. 4d. It can be seen from the figure that the isotope ion peaks of [Cu(Ame-H)(DMSO)]⁺ are m/z 678.0252, m/z 679.0285, m/z 680.0234, m/z 681.0267, m/z 682.0301, respectively, which are highly matched with the isotope mass spectrum peak of the quasi-molecule ion peak m/z 678.0256. Therefore, it can be confirmed that the ion corresponding to the ion peak m/z 678.0256 is [Cu(Ame-H)(DMSO)]⁺. Similarly, the ion corresponding to the ion peak m/z 826.0636 (FIG. 4e) is [Cu(Ame-H)(DMSO)₂]⁺. In summary, Ame and $Cu^{2+}$ form a complex having a ratio of 1:1. The coordination sites where Ame forms complex with $Cu^{2+}$ are confirmed to be 5-OH, 4-C=O, 5"-OH and 4"-C=O by IR spectrum and UV-vis spectrum. Since the activity of 5"-OH is higher than that of 5-OH, the coordination sites where Ame forms complex with $Cu^{2+}$ are the most likely to be 5"-OH and 4"-C=O. Therefore, the most likely structural formula of [Cu(Ame-H)(DMSO)]⁺ and [Cu(Ame-H)(DMSO)₂]⁺ are as follows:

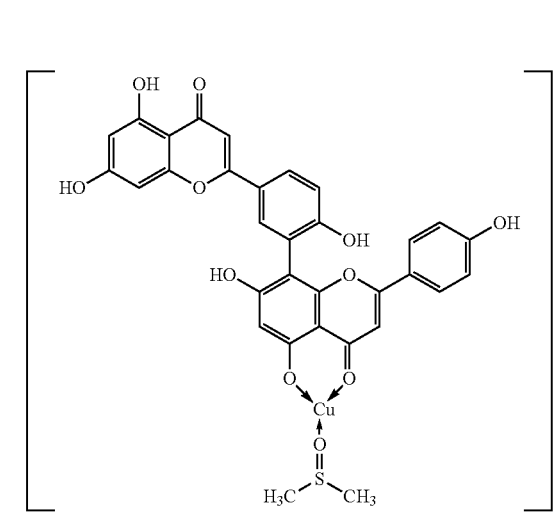

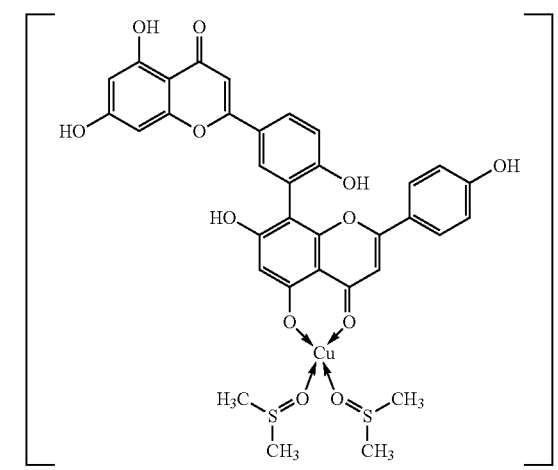

It can be found that the structural formula of [Cu(Ame-H)(DMSO)]⁺ is similar to that of [Cu(Ame-H)(DMSO)₂]⁺, the only difference is that the numbers of DMSO molecular contained are different. The reason is the ion [Cu(Ame-H)(DMSO)₂]⁺ lost a DMSO molecular under the voltage of the instrument. Therefore, the structure of the complex ion is [Cu(Ame-H)(DMSO)₂]⁺. In addition, since the metal salt in the experiment is a nitrate or a hydrochloride, the complex contains nitrate or chloride ions. Therefore, the structural formula of the Ame-Cu complex is as follows:

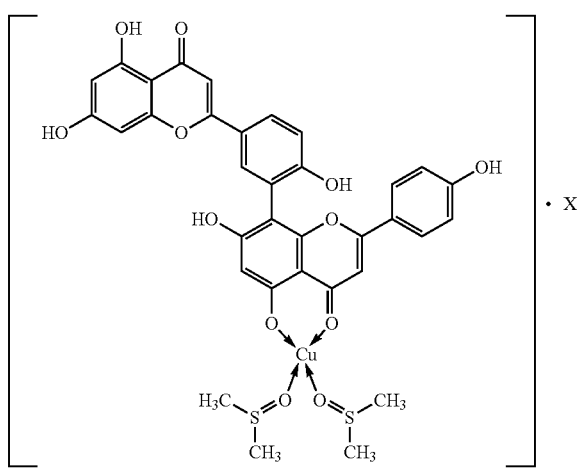

X is NO$_3^-$ or Cl$^-$.

Embodiment 10

The antitumor activity of Ame and Ame-Cu complex were studied by MTT method with the following process:

(1) the HepG2 and HeLa cell suspensions were inoculated into 96-well culture plate, 100 μL was added for each well, (1×10$^5$/mL), and then cultured in a 5% CO$_2$ incubator at 37° C. for 24 h;

(2) after culturing for 24 h, the supernatant was discarded, 100 μL of pre-diluted sample was added, 10 replicate wells were set for each concentration, and then incubated in the 5% CO$_2$ incubator for 24 h; meanwhile, control wells (DMSO, cell suspension, MTT), and blank wells (medium, DMSO, MTT) were set;

(3) After culturing for 36 h, the supernatant was discarded, 100 μL of DMEM medium containing MTT (5 mg/mL) were added, and then continuously cultured for 4 h;

(4) After 4 h, the supernatant was carefully scavenged, 200 μL of DMSO was added to each well, adequate shaking was performed for 15 min in a constant temperature oscillator, the absorbance was measured at 595 nm by a microplate reader, the inhibition rates of the sample to HepG2 and HeLa cells were calculated by OD, and the half-inhibitory concentration IC$_{50}$ value was calculated by using the modified Karber formula.

$$IR = 1 - \frac{OD_1}{OD_0} \quad \text{(Formula 1)}$$

$$lgIC_{50} = Xm - I(P - (3 - Pm - Pn)/4) \quad \text{(Formula 2)}$$

Where, IR is the inhibition rate, OD$_0$ is the absorbance of the control group, OD$_1$ is the absorbance of the sample group, Xm is 1 g (the maximum dose), I is 1 g (the maximum dose/adjacent dose), P is the sum of positive reaction rates, Pm is the maximum positive reaction rate, and Pn is the minimum positive reaction rate.

Figure 5:
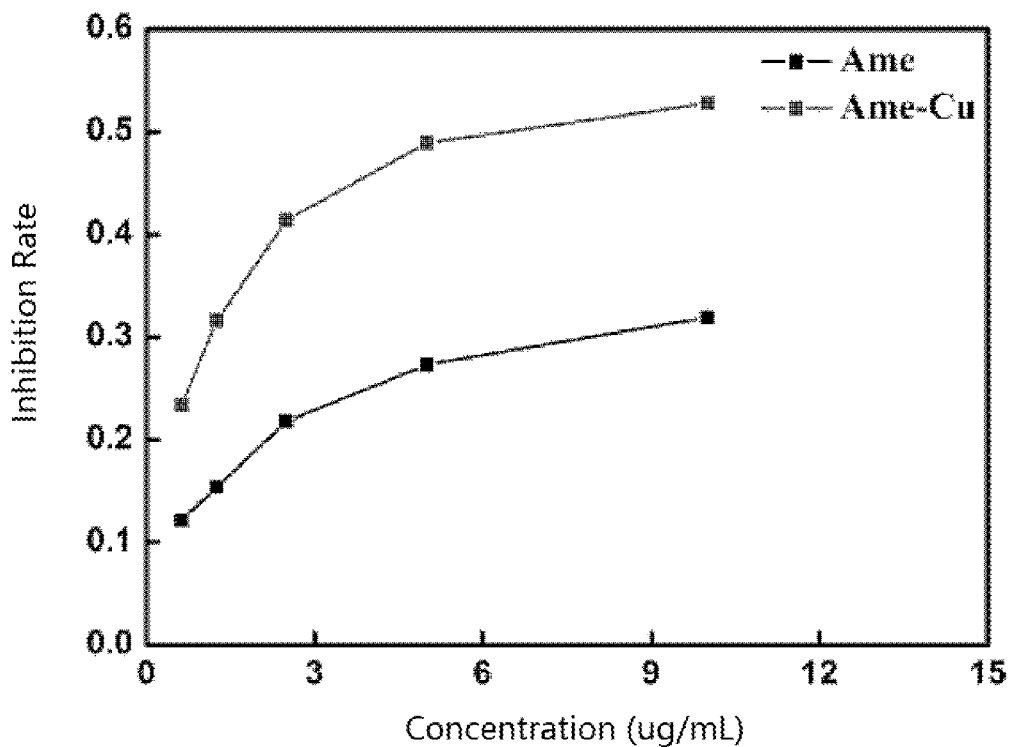
FIG. 5 is a diagram showing results of inhibition effects of an Ame and an Ame-Cu complex on HegG2 cells.
Figure 6:
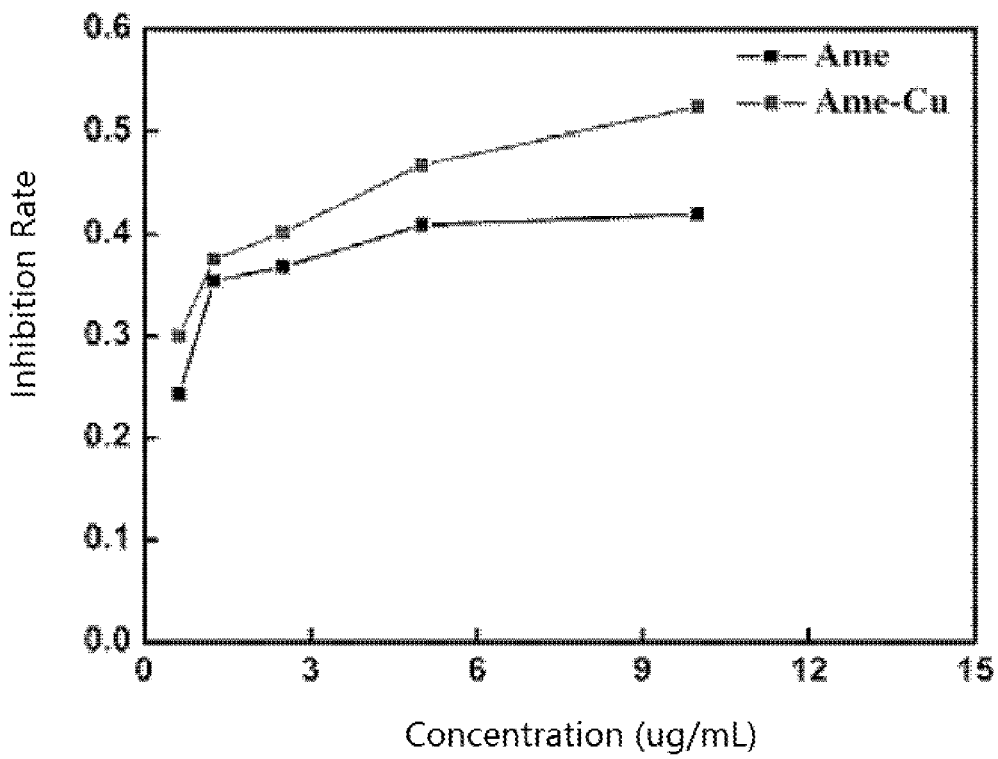
FIG. 6 is a diagram showing results of inhibition effects of an Ame and an Ame-Cu complex on HeLa cells.
Figure 7:
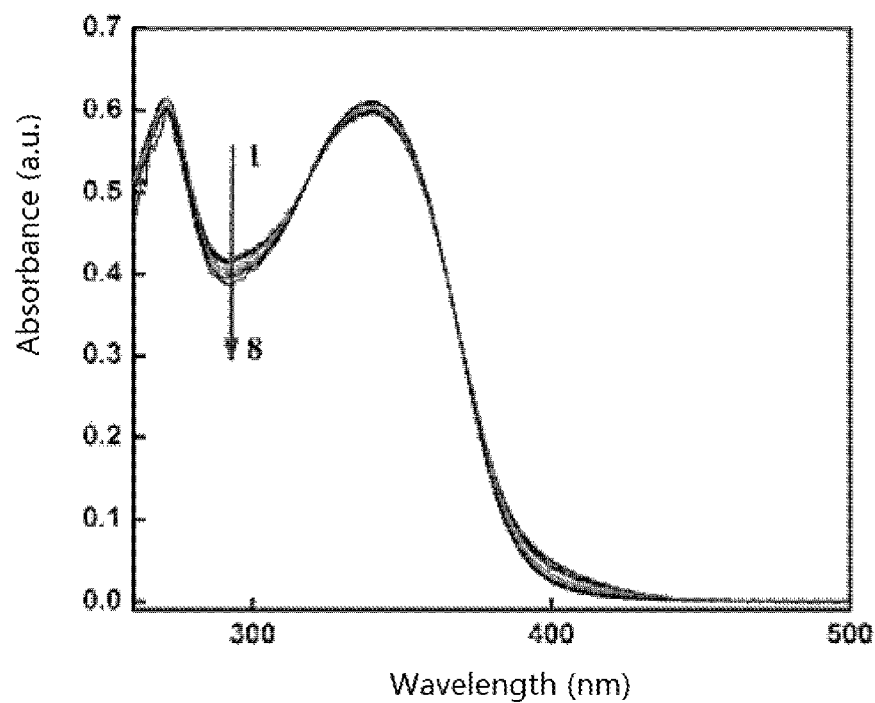
FIG. 7 is a diagram showing a result of an effect of fDNA on the UV-vis spectrum of the Ame.
Figure 8:
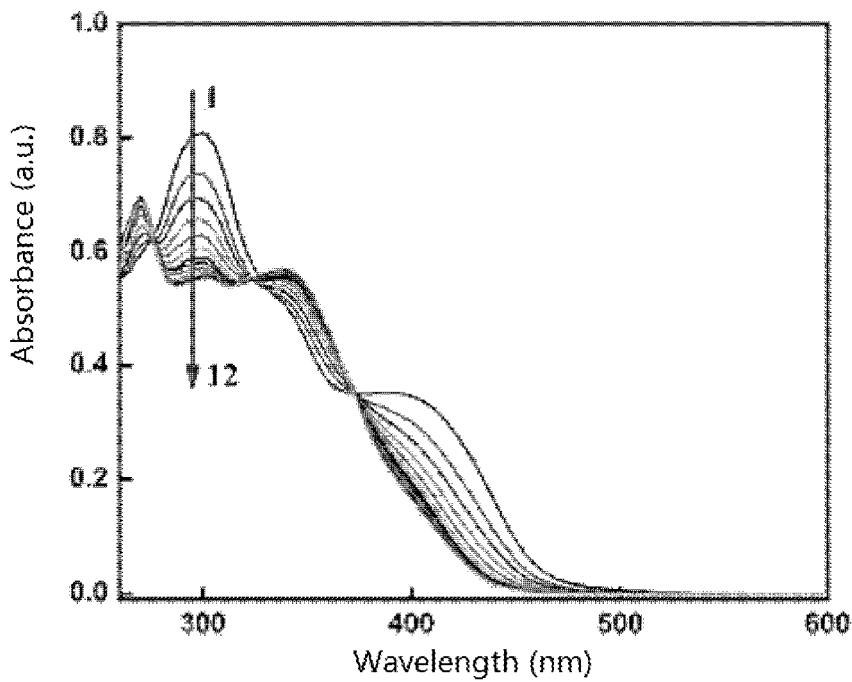
FIG. 8 is a diagram showing a result of an effect of fDNA on the UV-vis spectrum of the Ame-Cu complex.
Figure 9:
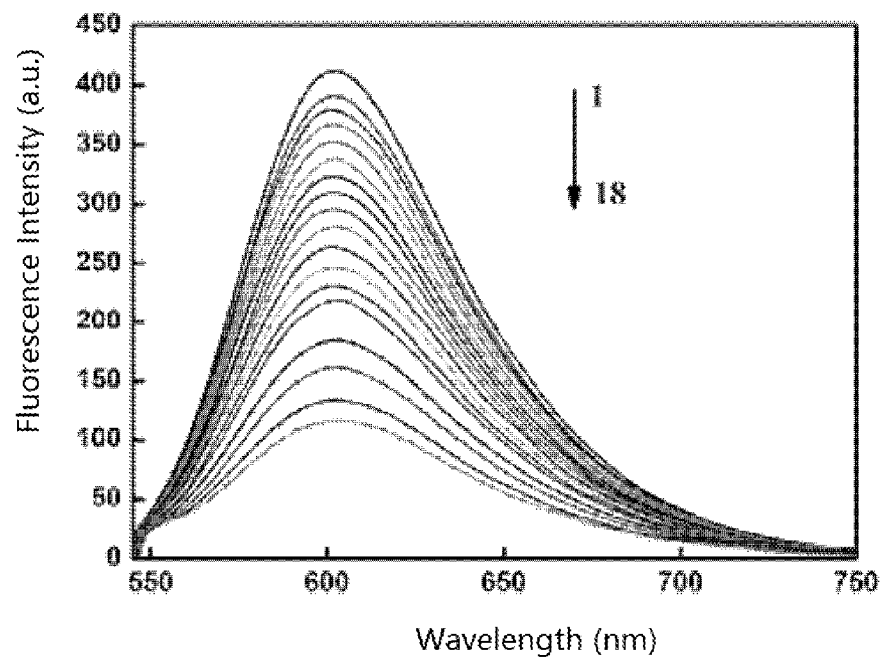
FIG. 9 is a diagram showing a result of an effect of an Ame on a fluorescence emission spectrum of an fDNA-EB system.
Figure 10:
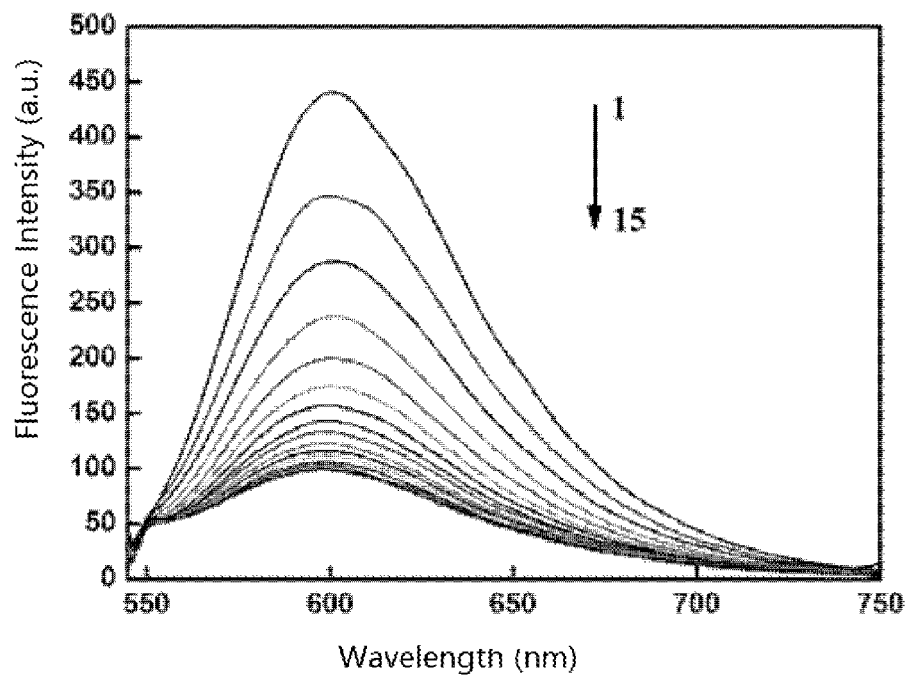
FIG. 10 is a diagram showing a result of an effect of an Ame-Cu complex on a fluorescence emission spectrum of an fDNA-EB system.
Figure 11:
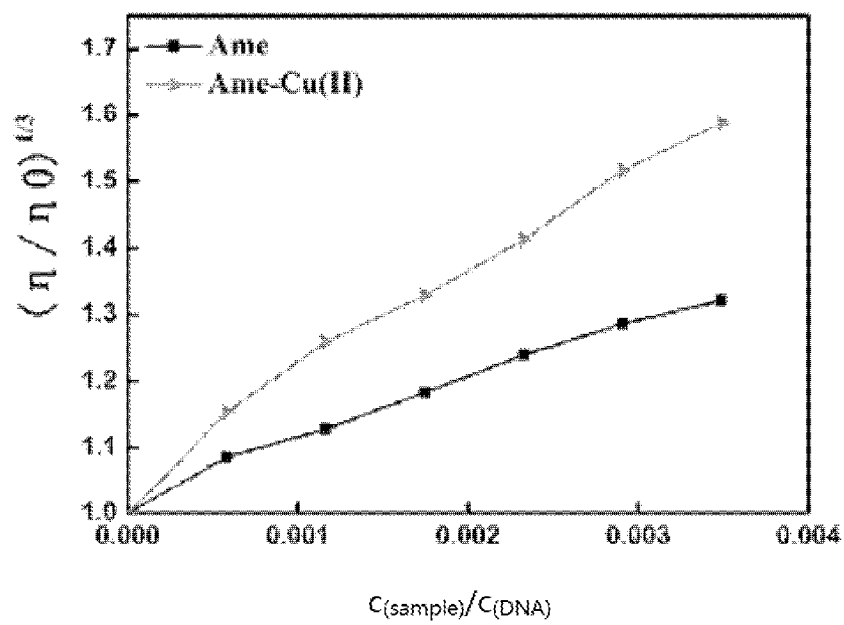
FIG. 11 is a diagram showing a result of an effect of an Ame and an Ame-Cu complex on a viscosity of an fDNA solution.
Figure 12:
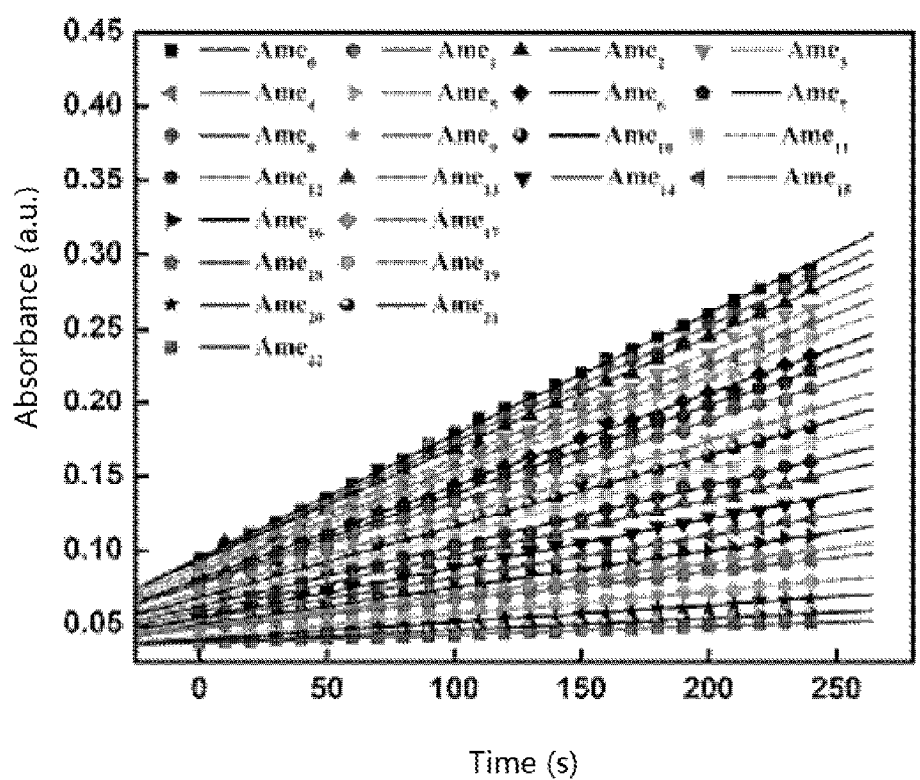
FIG. 12 is a diagram showing a result of an effect of an Ame on an auto-oxidation rate of pyrogallol.
Figure 13:
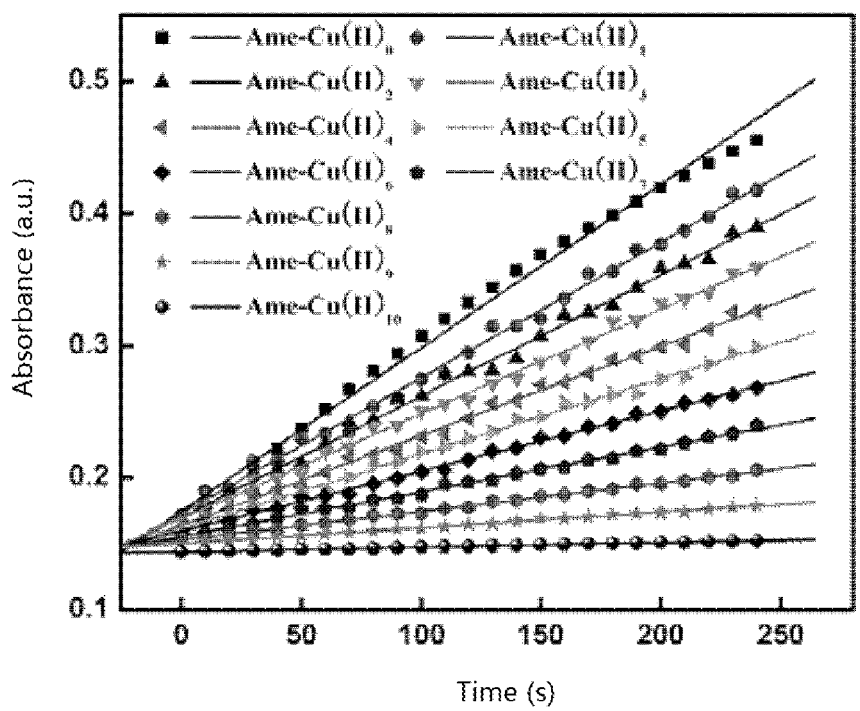
FIG. 13 is a diagram showing a result of an effect of an Ame-Cu complex on an auto-oxidation rate of pyrogallol.
Figure 14:
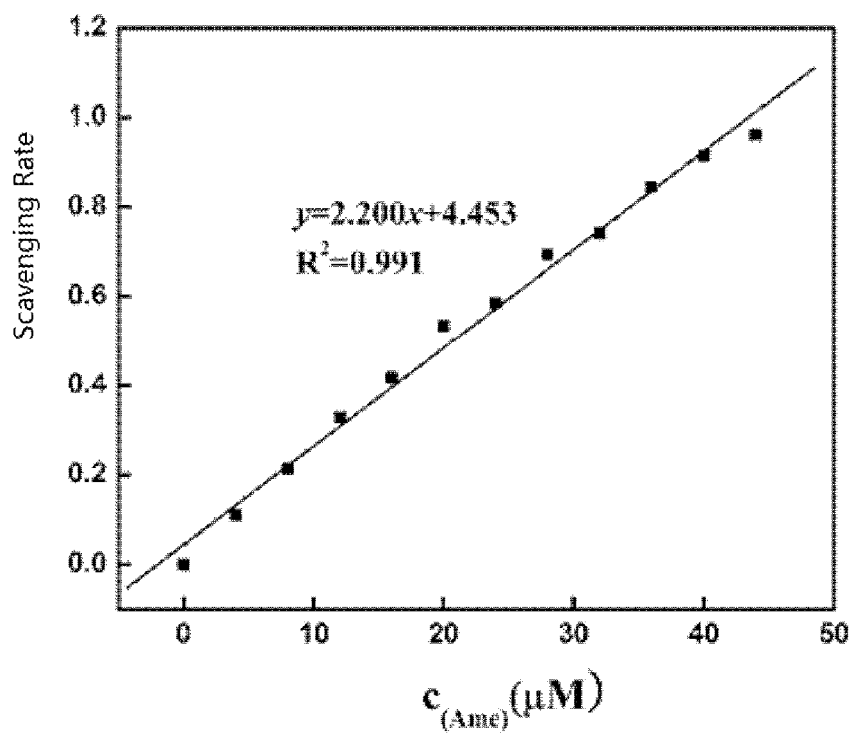
FIG. 14 is a diagram showing a result of an $ABTS^+$. free radical scavenging ability of an Ame.
Figure 15:
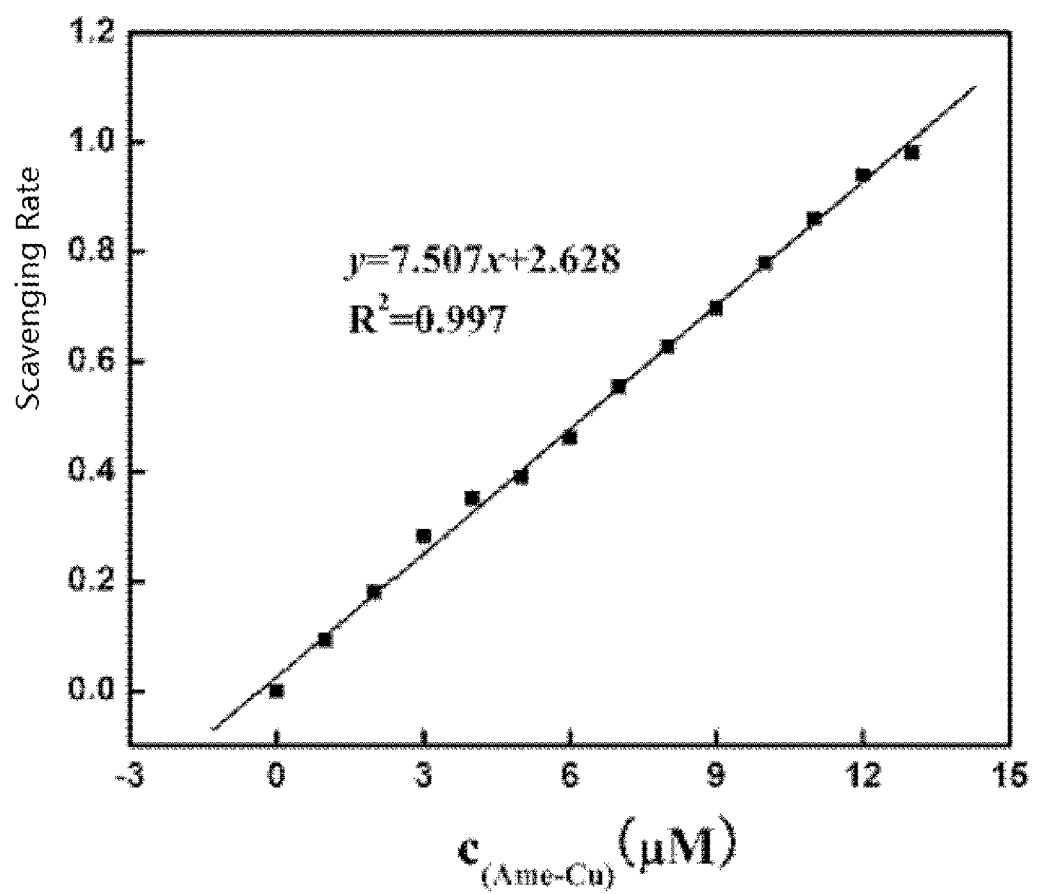
FIG. 15 is a diagram showing a result of an $ABTS^+$. free radical scavenging ability of an Ame-Cu complex.

The results are shown in FIGS. 5-6. It is found that Ame-Cu complex can effectively inhibit the growth of the hepatoma cells HepG2 and the cervical cancer cells HeLa, IC$_{50}$ values thereof are 5.638 and 5.247 μmol·L$^{-1}$, respectively, which are smaller than the IC$_{50}$ values of the Ame (The IC$_{50}$ values of Ame are 13.633 and 8.040 μmol·L$^{-1}$, respectively), indicating that the Ame-Cu complex has better antitumor activity than the Ame. UV-vis spectroscopy, fluorescence spectroscopy and viscosity method are used to study the interaction between the Ame and herring sperm DNA (fDNA), and the interaction between the Ame-Cu complex and herring sperm DNA (fDNA), to further reveal the mechanism of antitumor activity, the obtained spectra are shown in FIGS. 7-11. The results show that the interaction between the Ame and the fDNA, and the interaction between the Ame-Cu complex and the fDNA are both in the intercalation manner, and the interaction between the complex and the fDNA is stronger than that between the Ame and the fDNA. Thereby, it can be speculated that the mechanism of antitumor activity of the Ame and its complex may be that Ame or the complex thereof enters the interior of the cell and intercalates with the DNA strand to cause apoptosis. Since the interaction of the complex with DNA is stronger than of the Ame, the antitumor activity thereof is also stronger than of the Ame.

Embodiment 11

The free radical scavenging capability of the Ame and the Ame-Cu complex were studied by pyrogallol auto-oxidation method and ABTS method with the following steps:

(1) Pyrogallol Auto-Oxidation Method

Determination of auto-oxidation rate V$_0$ of pyrogallol: 2 mL Tris-HCl buffer (pH=8.20) was added to a 10 mL sample tube at 25° C., 100 μL DMSO was added as a control, after adding 0.8 mL distilled water, 0.2 mL pyrogallol solution having a concentration of 2 mmol·L$^{-1}$ was added, the mixture was poured into a cuvette after mixing uniformly, the absorbance at 322 nm was measured with pure water as a blank, the A value was recorded every 10 s for a total of 4 min, linear regression was performed with t as the abscissa, and A as the ordinate, straight line slope thereof is V$_0$, and the measurement was performed for three times to obtain an average value.

Determination of auto-oxidation rate V$_1$ of pyrogallol after adding sample: 2 mL Tris-HCl buffer (pH=8.20) was added to a 10 mL sample tube at 25° C., 100 μL samples of various concentrations that were dissolved in DMSO were added, after adding 0.8 mL distilled water, 0.2 mL pyrogallol solution having a concentration of 2 mmol·L$^{-1}$ was added, the mixture was poured into a cuvette after mixing uniformly, the absorbance at 322 nm was measured with double distilled water as a blank, the A value was recorded every 10 s for a total of 4 min, linear regression was performed with t as the abscissa, and A as the ordinate, straight line slope thereof is V$_1$, and the measurement was performed for three times to obtain an average value. The free radical scavenging rate was calculated according to Formula 3.

$$SR(\%) = (1 - v_1/v_0) \times 100\% \quad \text{(Formula 3)}$$

(2) ABTS Method

Determination of ABTS$^+$. free radical ion scavenging capability of the blank sample: at 25° C., 2.9 mL ABTS$^+$. free radical ion working solution was added into a 10 mL sample tube, 100 μL DMSO was added, after reacting for 5 min, the UV-vis spectrum was measured, and the absorption intensity A$_0$ at 730 nm was recorded.

Determination of ABTS$^-$. free radical ion scavenging capability of the samples: at 25° C., 2.9 mL ABTS$^+$. free radical ion working solution was added into a 10 mL sample tube, 100 μL samples of different concentrations that were dissolved in DMSO were added, after reacting for 5 min, the UV-vis spectrum was measured, and the absorption intensity A$_1$ at 730 nm was recorded, and the ABTS$^+$. free radical ion scavenging rate was calculated according to Formula 4.

$$SR(\%) = (1 - A_1/A_0) \times 100\% \quad \text{(Formula 4)}$$

As shown in FIGS. 12-15, the results of pyrogallol auto-oxidation method show that the IC$_{50}$ of the Ame and the Ame-Cu complex to scavenge O$_2^-$. free radical are 23.273 μmol·L$^{-1}$ and 4.5683 μmol·L$^{-1}$, and it can be found that the O$_2^-$. free radical scavenging capability of the Ame-Cu complex is significantly stronger than that of the Ame.

The ABTS+. free radical scavenging capabilities of the Ame and the Ame-Cu complex are concentration dependent. Within a certain range, the scavenging rate is linear with the concentration. The curve of the scavenging rate and the concentration (c) is plotted in the present invention to obtain a corresponding linear equation, and the maximum half-inhibitory concentration ($IC_{50}$ value) is calculated. The $IC_{50}$ values of the Ame and the Ame-Cu complex for scavenging ABTS+. free radicals are 20.703 and 6.310 $\mu mol \cdot L^{-1}$, respectively. It can be seen that the ABTS+. free radical scavenging capability of the Ame-Cu complex is significantly stronger than that of the Ame.

The amentoflavone-copper complex is first synthesized by the method of the present invention, and the antitumor activity and the antioxidant activity thereof are studied. It is found that the antitumor activity and the antioxidant activity of the complex are both stronger than that of the biflavone itself. The research work of the biflavone complex is developed, which provides important reference value for the development of new drug.

What is claimed is:

1. A biflavone-copper complex, comprising the following structural formula:

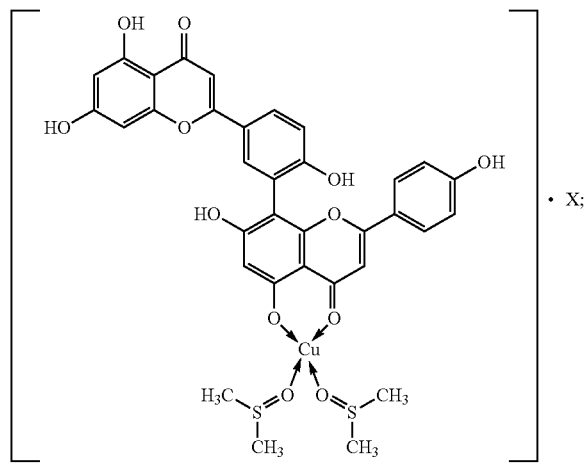

wherein, X is $NO_3^-$ or $Cl^-$.

2. A method of preparing the biflavone-copper complex of claim 1, comprising the following steps: dissolving a copper salt in an alcohol to obtain a first solution, adding the first solution into a biflavone alcoholic solution to obtain a second solution, and controlling a pH of the second solution to 5-7; under a heating and a stirring, performing a reaction on the second solution for 2-5 h to form a precipitate; filtering the precipitate to obtain a filtered precipitate, washing the filtered precipitate with alcohol and water to obtain a washed precipitate, recrystallizing the washed precipitate using dimethyl sulfoxide as a solvent to obtain a recrystallized precipitate, and drying the recrystallized precipitate to obtain the biflavone-copper complex.

3. The method of preparing the biflavone-copper complex of claim 2, wherein a biflavone of the biflavone alcoholic solution is an amentoflavone.

4. The method of preparing the biflavone-copper complex of claim 2, wherein the copper salt is copper nitrate or copper chloride.

5. The method of preparing the biflavone-copper complex of claim 2, wherein the pH of the second solution is adjusted with an alkali alcoholic solution, and an alkali used in the alkali alcoholic solution comprises sodium hydroxide, potassium hydroxide, aqueous ammonia, sodium ethoxide, and sodium methoxide.

6. The method of preparing the biflavone-copper complex of claim 2, wherein the reaction is performed at a temperature of 30° C.-50° C., and a reaction time is 2-5 h.

7. The method of preparing the biflavone-copper complex of claim 2, wherein a molar ratio of a biflavone to a copper ion in the second solution is 2-2.5:1.

8. The method of preparing the biflavone-copper complex of claim 2, wherein the solvent used in the recrystallization is dimethyl sulfoxide, and a drying method is a freeze-drying or a low temperature vacuum-drying.

* * * * *